(12) United States Patent
Xiang et al.

(10) Patent No.: US 6,693,426 B1
(45) Date of Patent: Feb. 17, 2004

(54) SPATIALLY RESOLVED SPIN RESONANCE DETECTION

(75) Inventors: Xiao Dong Xiang, Alameda, CA (US); Gang Wang, Albany, CA (US); Haitao Yang, Albany, CA (US); Gerald F. Dionne, Winchester, MA (US)

(73) Assignee: Intematix Corporation, Moraga, CA (US)

( * ) Notice: Subject to any disclaimer, the term of this patent is extended or adjusted under 35 U.S.C. 154(b) by 0 days.

(21) Appl. No.: 10/071,563

(22) Filed: Feb. 9, 2002

(51) Int. Cl.[7] .................................. G01V 3/00
(52) U.S. Cl. ....................... 324/300; 324/304
(58) Field of Search ..................... 324/304, 300, 324/301, 305, 302, 637; 600/420

(56) References Cited

U.S. PATENT DOCUMENTS 6,311,086 B1 * 10/2001 Ardenkjaer-Larsen ...... 600/420
6,472,869 B1 * 10/2002 Upschulte et al. .......... 324/304
6,538,454 B1 * 3/2003 Frenkel et al. .............. 324/637

* cited by examiner

*Primary Examiner*—Diego Gutierrez
*Assistant Examiner*—Brij B. Shrivastav
(74) *Attorney, Agent, or Firm*—John F. Schipper

(57) ABSTRACT

Methods for spatially resolve spin resonance detection in a sample of material, with a resolution as small as 0.5 $\mu$m–1 mm. In one embodiment, a coupler having at least one pair of degenerate orthogonal modes provides an evanescent input signal along one coupler axis to the sample, to which a magnetic field is applied, and senses a spin interaction signal along another coupler axis. In another embodiment, an evanescent input signal is applied to the sample along one of two identical transmission line resonators, and a difference of the two resonator signals provides a spin interaction signal. In another embodiment, a polarized laser beam provides an evanescent input signal to the sample, and the spin interaction signal is sensed according to a second beam polarization direction. Certain ferromagnetic or ferrimagnetic molecules, such as YIG, can be used to tag selected chemical and biological molecules, using spatially resolved spin resonance detection for interrogation.

34 Claims, 8 Drawing Sheets

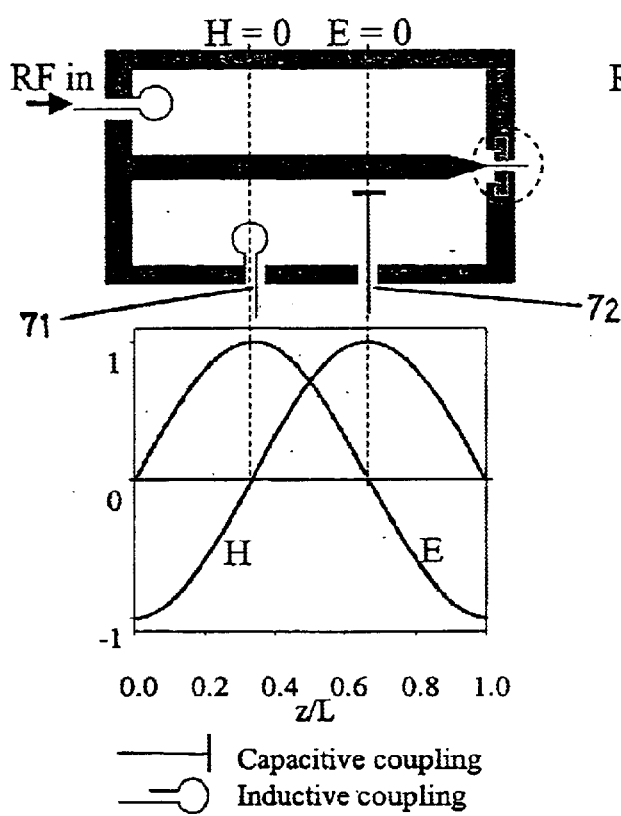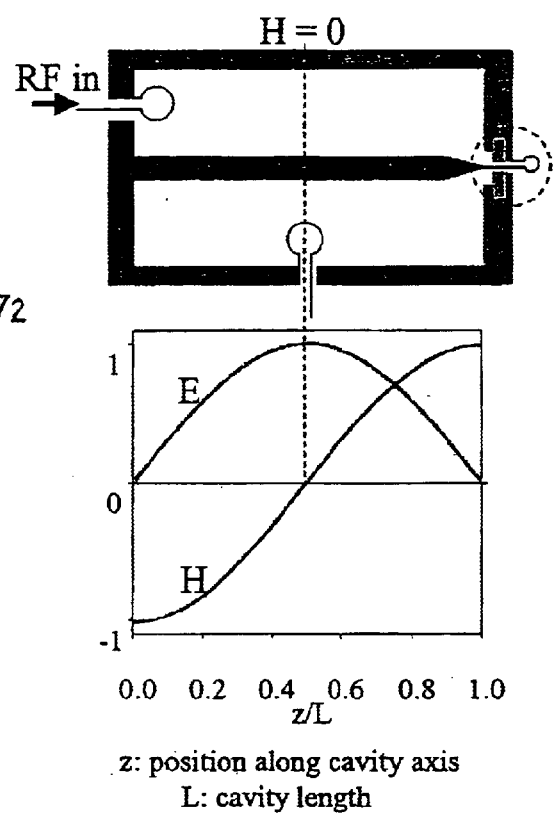
Fig. 7A
Fig. 7B

SPATIALLY RESOLVED SPIN RESONANCE DETECTION

FIELD OF INVENTION

This invention relates to the designs of spatially resolved spin resonance detection, including but not limited to electron spin resonance (ESR) and nuclear spin resonance (NMR), with high sensitivity.

BACKGROUND OF THE INVENTION

For many applications in materials and bioscience research, spatially resolved spin resonance detection with high sensitivity is desired. Conventional spin resonance detection experiments are usually performed by placing a sample in a microwave cavity or a pair of RF coils situated in a strong DC or substantially static magnetic field that is perpendicular to the microwave or RF magnetic field. High power microwave or RF radiation excites the coherent spin precession. Precessing spin-induced induction and absorption signals are picked up by cavity or coil and detected by diode mixer. Although the intrinsic sensitivity is limited by cavity Johnson noise, which is near single-spin detectivity, this level of detection has never been possible practically. Primary limitations in a conventional experiment are large background noise from high power excitation signal generated by high-power klystron source (need to excite spin in bulk samples) and diode detector noise since low noise amplifier cannot be employed before diode detector without being saturated by high level excitation signal pick up at detection port.

What is needed is an approach that provides spin resonance detection, preferably spatially resolved to within 0.5 $\mu$m to 1 mm. Preferably, the approach should avoid detection of background signals, such as the strong input or excitation signal, and should not require use signal levels that are at or above a saturation threshold.

SUMMARY OF THE INVENTION

These needs are met by the invention, which provides methods and systems that allow evanescent microwave or RF wave excitation and detection of spin resonance and cancellation of excitation signal at the detection port, and therefore allow spatially resolved (with spatially resolution better than the wavelength of the excitation signal) spin resonance detection with high sensitivity limited by the low noise amplifier or Johnson noise of the resonator.

In a first embodiment, an evanescent microwave orthogonal resonator probe is designed to achieve high spatial resolution and high sensitivity spin resonance detection. The probe design uses a bimodal transmission-type (or waveguide/cavity type) resonator with input and output coupled to orthogonal modes. The purpose of the design is to isolate excitation and detection modes and dramatically reduce background signal. This will allow low noise amplification to be implemented to achieve Johnson noise limited sensitivity without amplifier saturation. Only a very small spin resonance induced signal power is coupled to the probe output and amplified. Spin resonance signal is proportional to excitation RF or microwave field intensity $(H_{rf})^2$ below saturation threshold. In conventional spin resonance studies, very high power (klystron source) is required to reach the saturation level. In this design, only very small microwave power is needed to excite small volume of sample near the tip (or aperture) with very high field intensity. This will dramatically reduce the background noise of microwave source because a low noise level generator can be used. Because both excitation and pickup volume are small, other extrinsic noises will also be dramatically reduced. A typical klystron source has FM noise around -30dB while a high quality microwave synthesizer proposed to implement in this project has FM noise around -110dB.

In a second embodiment, internal or external cancellation schemes are used to cancel the large excitation signal that would otherwise be detected at the detection port. In an external cancellation scheme, two substantially identical transmission line resonators (or cavity/waveguide resonators) with the same resonant frequency and insertion loss are used. One of the resonators has an evanescent wave probe to interact with sample (excite and detect spin resonance). The evanescent probe may be (1) a metal tip connected to the center conductor of a transmission type resonator, (2) a metal loop connected between the center conductor and ground shielding; or (3) an aperture on the shielding wall of a cavity or waveguide resonator. The other resonator serves as a reference or "dummy" resonator. The outputs of the two resonators are received by a power combiner with a 180° phase-shift for one of the input signals, thereby forming a difference of the output signals. This signal combiner cancels the large background (excitation) signal, and a low noise amplifier can be employed to increase the sensitivity. As the evanescent probe excites the spin resonance, the probe-sample interaction breaks the symmetry and precise cancellation, and the resulting small changes represent the spin resonance signal to be detected.

In the case of internal cancellation scheme, the pick up coupling will be positioned at the node of the mode of either a transmission type or cavity type resonator, equipped with evanescent probe as described above. As the evanescent probe excites the spin resonance, the induced magnetization will change the node position in the resonator. As a consequence, the pick up coupling will detect the small signal due to this spin resonance induced effect without coupling to the large excitation background signal. Low noise amplifier can then boost the signal to achieve high sensitivity in both cases.

In each of these situations, in order to further increase the sample volume sensitivity, (e.g., increase the spin states population difference, especially for NMR at room temperature), optical pumping is preferably used. An integrated optical path is designed to apply optical pumping.

In a third embodiment, an optical pumping and detection scheme is employed, using an evanescent electromagnetic wave excitation. The integrated evanescent microwave probe-optical microscope system (EMP-OM) can provide microwave induced optical detection for optically pumped spin resonance detection. Spatial resolution in both operating modes is achieved by an evanescent microwave (or radio wave) probe, which only excites and picks up spin resonance induced microwave (or RF) induction and absorption signals in a very small sample volume (as small as nm$^3$) proportional to the cube of probe radius.

BRIEF DESCRIPTION OF THE DRAWINGS

FIGS. 7 and 8 illustrate an internal cancellation scheme (transmission type and cavity type resonator, respectively), where the pickup coupling is positioned at the node of resonance mode of the resonator.

DESCRIPTION OF THE BEST MODES OF THE INVENTION

Figure 1:
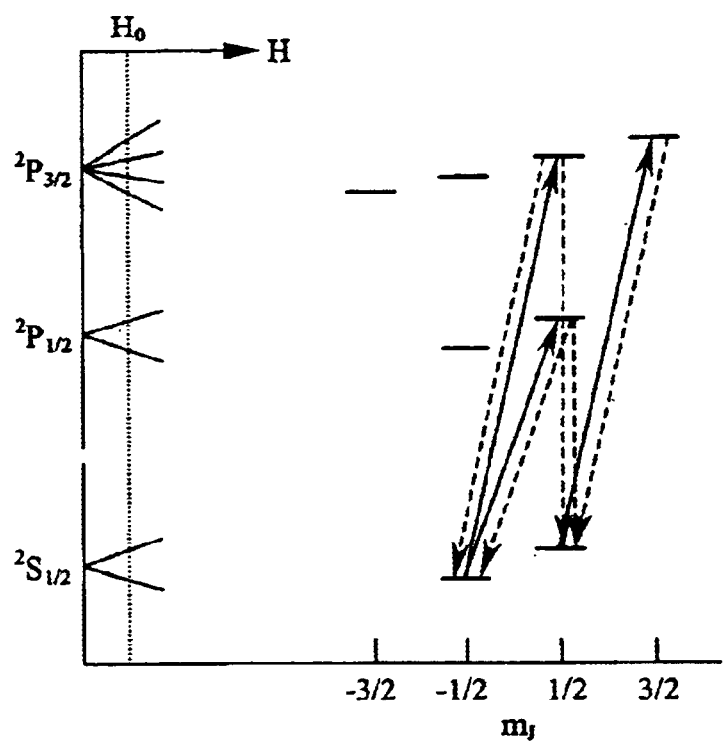
FIG. 1 graphically illustrates fine structure of the resonance radiation states for a typical alkali metal.

One way to improve the detection sensitivity is to employ a resonator with degenerate orthogonal modes. In this case, input and output channels are coupled to these orthogonal modes respectively. Ideally, the pick up coupling only picks up signal due to spin resonance induced effects from the sample, not from the large excitation signal. Ideally, because the power fed from input channel will not coupled to the output channel, one gets a near zero-power background. The low noise amplifier can therefore be employed without being saturated. When the magnetic resonance is excited, the resonance destroys the symmetry of those orthogonal modes and couples small power to the mode that is coupled with output channel. This small power due to the symmetry breaking is the signal power that desired to be detected. Witte et al. reported a design of an X-band induction spectrometer with a bimodal cavity with 110 dB isolation between transmitter and receiver [A. Witte, G. Laukien and P. Dullenkopf, *Appl. Phys.* 2, 63–70 (1973)]. Wallace and Silsbee have also demonstrated a microstrip resonator for thin film measurement [W. J. Wallace and R. H. Silsbee, RSI 62 (7), 1754 (1991)]. However, in these studies only bulk samples or large area thin film samples are involved.

In a different direction, spatially resolved spin resonance detection has been attempted by employing evanescent electromagnetic wave detector [R. F. Soohoo, J. of Applied Physics, Vol. 33, 1276 (1962) and Masahiro Fursawa and Motoji Ikeya, J. of the Physical Society of Japan, Vol. 59, 2340 (1990)]. The basic approach in these studies is to radiate the sample local area with evanescent electromagnetic wave from an aperture on the wall of microwave resonator in applied DC magnetic field. The resolution achieved is around mm range and the sensitivity is relatively low.

In another different direction, optical spin resonance pumping and detection has been developed. One of the major problems for spin resonance detection is the small population difference that exists between two adjacent Zeeman levels governed by Boltzmann statistics:

$$\Delta n = 1 - \exp\left(-\frac{g\mu B}{kT}\right), \quad (1)$$

where g is gyromagnetic ratio, $\mu$ is the nuclear magneton $\mu_N$ for NMR, or Bohr magneton $\mu_B$ for ESR. At room temperature and in 5 Tesla magnetic field, this corresponds to $10^{-5}$ for a typical NMR and $10^{-2}$ for ESR experiment. Only a very small fraction of spin available in a sample volume can be excited by applied microwave or RF field and detected even using the most sensitive detector. This fact explains why it is difficult to detect spin resonance signal from a sample volume, which contain a small number of spins (since there are only one out of $10^5$ spins that will absorb net microwave power at room temperature). One method to get around this problem is optical pumping.

Optical pumping refers to the redistribution of atoms among their fine or hyperfine structure levels by means of light. This was first observed by J. Brossel, A. Kastler and J. Winter [J. Brossel, A. Kastler, J. Winter, *J Phys. Radium* 13, 668 (1952)], following suggestions by A. Kastler [A. Kastler, *J Phys. Radium* 11, 255 (1950). Optical pumping is usually performed with circularly polarized light. Just as light exerts radiation pressure, circularly polarized light can transfer angular momentum and produce a torque.

To understand the effect of optical pumping on the atoms, consider a simple experiment. FIG. 1 is a simplified energy-level diagram of a typical alkali metal. Consider an atom with a nucleus that has no nuclear spin and no magnetic momentum. In the ground state (or S state) the electron has no orbital angular momentum so that the angular momentum of the entire structure is solely the spin of the outer valence electron, which can be quantized in a direction parallel ($m_{j=}\frac{1}{2}$) or antiparallel ($m_{j=}-\frac{1}{2}$) to an external magnetic field. The circularly polarized light induces transitions from this S ground state to a P level, which has one unit of orbital angular momentum. Through the spin-orbit interaction, this level is split into two levels, for which the total angular momentum J is either $\frac{3}{2}$ or $\frac{1}{2}$, depending on the orientation of the electron spin with respect to its orbital motion. And in each level, 2J+1 sublevels are available, in which $m_j$ arranges from −J to J. The solid lines show the absorption process, which involves an increase of one unit of angular momentum when the atoms are irradiated with circularly polarized light along a selected axis. The dotted lines indicate the re-emission process, which can occur primarily by spontaneous emission and is therefore mostly unaffected by the absorbed light (although to some extent there are interesting interference effects between absorbed and emitted light).

After repeated fluorescence transitions of this kind, the atoms are stochastically shifted to occupy the higher quantum numbers m (or the lower ones, if the opposite direction of circular polarization is used) instead of following Boltzmann statistics. In the case of S-state atom with no nuclear spin, this is equivalent to saying that the valence electron is nearly 100% polarized, therefore dramatically increased the population difference in spin states.

Figure 2:
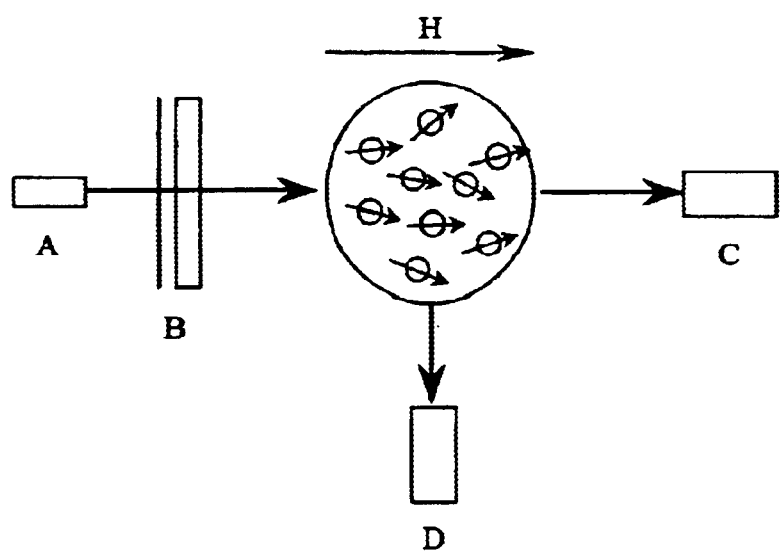
FIG. 2 schematically illustrates a simple optical pumping experiment, including a laser, a polarizer and quarter-wave plate, and one or more photodetectors FIGS. 3A and 3B schematically illustrate an orthogonal mode microstrip resonator with a tip to generate an evanescent wave signal and tip shielding structure.

Optical pumping also provides an optical detection mechanism for spin resonance in two ways, as illustrated in FIG. 2. When all atoms have been pumped into highest $m_j$ sublevel, the sample vapor will become transparent, and photodetector C will receive the full intensity of pumping light. Thus, observing the intensity of transmitted pumping light (transmission monitoring) is one important way to detect optical pumping. When complete optical pumping has occurred, there will no longer be any resonantly scattered light, and the intensity of fluorescent light at photodetector D will vanish. Consequently, pumping can also be detected by observing the fluorescent light through fluorescence monitoring.

If the nucleus of an atom used in optical pumping has a spin (denoted by a quantum number I) and a magnetic moment, in fields that are not too large, the magnetic moment of the nucleus will couple to the total angular momentum of the electron to form a new quantum number F, which ranges in unit steps of h between the sum of, and the difference between, J and I. In spite of the added complexity, optical pumping proceeds in exactly the same fashion as it does for the atom with electronic angular momentum only. It is therefore possible to do experiments with polarized nuclei (NMR) as well as with polarized electrons (ESR).

When combining optical pumping with the magnetic resonance technique, because an RF or microwave signal can induces hyperfine transitions of the atom in the magnetic field, which changes the electron distribution between the hyperfine levels, magnetic resonance will also have effect on the optical pumping. Thus, optical pumping not only can enhance the population difference between hyperfine levels, which will enhance the sensitivity of magnetic resonance detection, it also can be used as a detector of magnetic resonance transition. However, this method cannot be applied for conventional bulk sample spin resonance experiments due to lack of optical access for optical pumping and detection (e.g. samples are usually inside a microwave cavity).

In 1990, D. Raftery et al [D. Raftery et al, *Phys. Rev. Lett.* 66, 584 (1991)] used laser pumping to enhance the pulsed NMR signal of $^{129}$Xe, allowing the detection of low-pressure xenon gas and of xenon adsorbed on powdered solids. The workers observed an increase in sensitivity of more than two orders of magnitude over conventional NMR.

Several groups have claimed to observe magnetic resonance spectroscopy of a single molecule spin with optical detection. The methods used by these groups were not the same as, but were similar to, a conventional optical pumping technique. J. Kohler et al [J. Köhler et al, Science 268, 1457 (1995)] at the University of Leiden, Netherlands studied the individual pentacene-$d_{14}$ molecules doped into a p-terphenyl-$d_{14}$ host crystal by optically detected electron paramagnetic resonance spectroscopy. They mounted thin sublimation-grown crystals of p-terphenyl-$d_{14}$ containing about $10^{-8}$ mol of pentacene-$d_{14}$ per mol of p-terphenyl-$d_{14}$, which were cooled to 1.2° K between a LiF substrate and a quartz cover in the joint focus of a lens and a parabolic mirror. Even for these high quality crystals, the $S_1 \leftarrow S_0$ transition of pentacene is inhomogeneously broadened owing to the slight differences in the local environments of the guest molecules.

Exciting the system by a narrow band single-mode laser tuned far into the wing of this broadened transition, where the density of absorbers per unit frequency is very low, allows the detection of single molecules. The fluorescence emitted toward the red end of the absorption is collected by the parabolic mirror and recorded by photomultiplier and photon counting. When the molecule is excited into the $S_1$ singlet state, it can escape from the $S_0 \leftrightarrows S_1$ excitation-emission cycle to the lowest triplet state $T_1$, with a probability of 0.5 percent. Consequently, the fluorescence photons are emitted in bunches with an average dark period that corresponds to the mean residence time of the molecule in the triplet state. The three sublevels of $T_1$, labeled $T_x$, $T_y$, and $T_z$, are selectively populated and depopulated by intersystem crossing. Because levels $T_x$ and $T_y$ have a short lifetime and a high population probability compared to level $T_z$, the mean residence time of a molecule in the triplet state is prolonged under the influence of a microwave (RF) field in resonance with the ($T_x$-$T_z$) or ($T_y$-$T_z$) transition. This allows the observation of these magnetic resonance transitions as a decrease in fluorescence signal (fluorescence-detected magnetic resonance (FDMR)). J. Wrachtrup et al [J. Wrachtrup et al, Nature 363, 244 (1993)] in Germany and France have performed a similar experiment for optical detection of magnetic resonance in a single molecule.

The optical only technique does not have very high spatial resolution, which is limited by laser spot size. Although tapered optical fiber (near field optical probe) may give rise to better resolution in optical pumping, it will not be able to reach the power requirement of optical pumping due to waveguide decay problem.

Figure 3A:
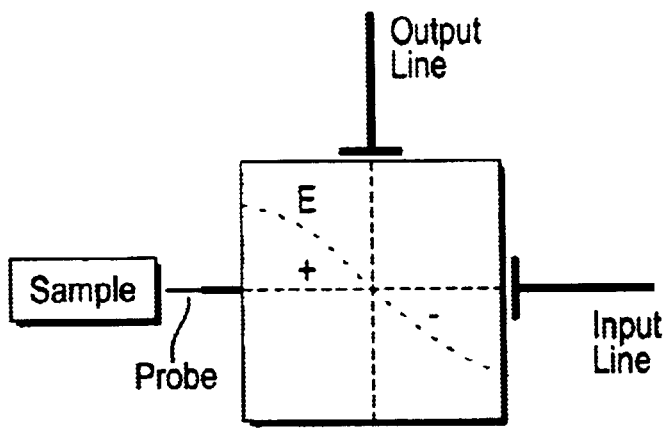
Figure 3B:
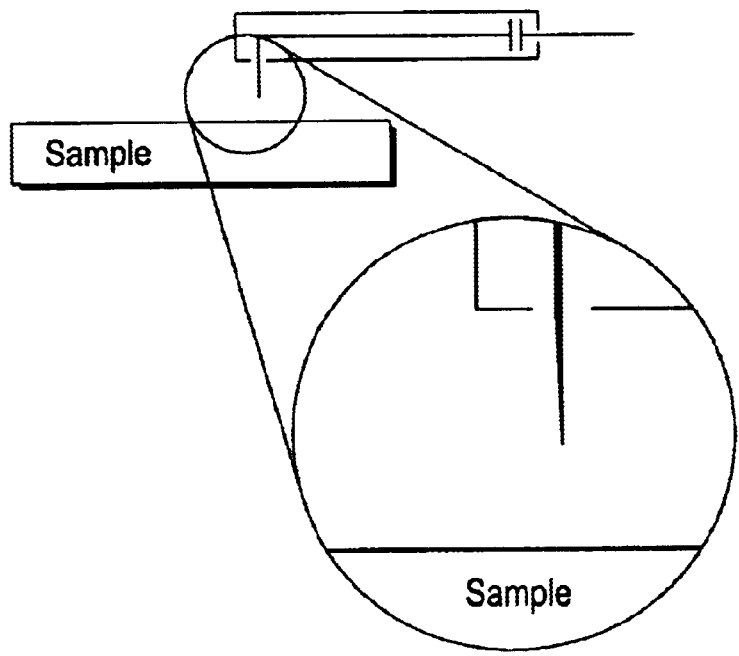

FIG. 3A and 3B schematically illustrate a square microstrip resonator or signal coupler, which is open at all four edges, and an associated shield structure for a probe tip. Both input and output transmission lines are coupled to the center of resonator edges with capacitance coupling and at right angle with each other. A probe tip is attached to the opposite side of input line. Because the coupler is square, some of the resonant modes will be degenerate. The electric-field nodal line of one of the pair of lowest-frequency modes is illustrated and the direction of the electric field is shown in the figure. The resonance mode orthogonal to this mode will have a nodal line at horizontal direction. Note that the output microstrip transmission line will not couple to the illustrated mode since the end of the transmission line is an equal-potential surface and is situated symmetrically with respect to the nodal line. Viewed from another perspective, if the described mode is excited, it will not induce any net charge on the end of the output transmission line. However, it will couple to the input transmission line so that power can be fed in from the input line without any power being coupled out to the output line. Optionally, one or more parameters associated with the output line can be adjusted so that, if a sample is not excited, the magnitude of a signal appearing on the output line is minimized (preferably with zero minimum). The square resonator or signal coupler shown in 3A can be replaced by a circular resonator, or by another resonator shape (e.g., a regular octagon) that has at least one set of (two or more) degenerate orthogonal modes.

Figure 4A:
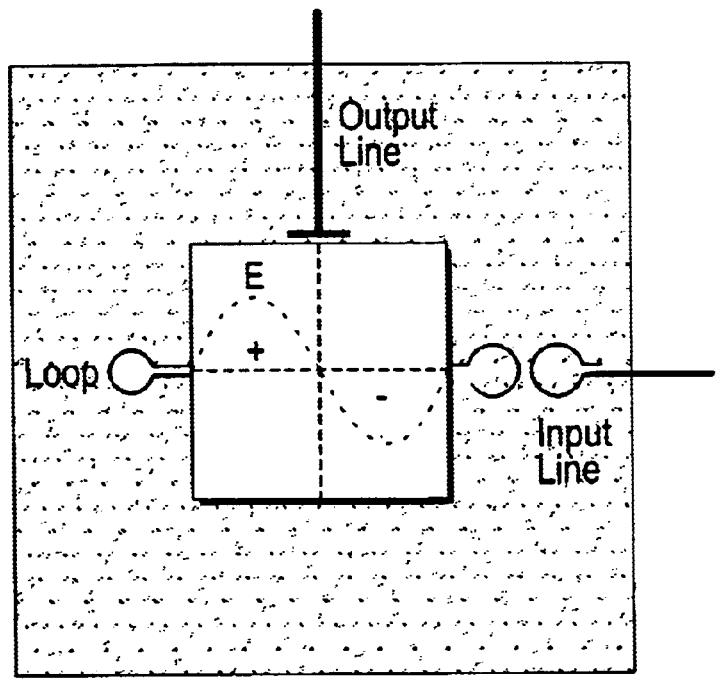
FIGS. 4A and 4B schematically illustrate an orthogonal mode microstrip resonator with loop tip to generate an evanescent wave and an associated shielding structure.
Figure 4B:
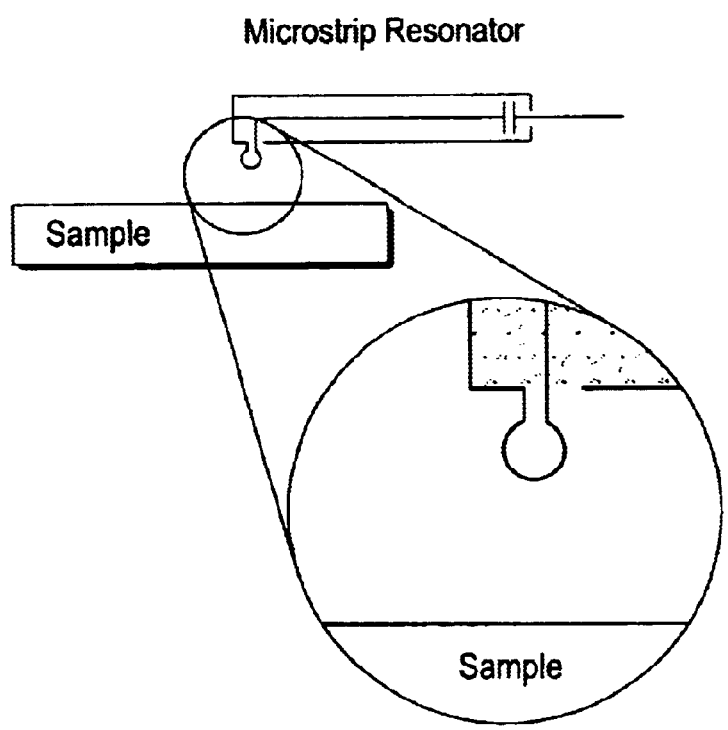

FIG. 4A illustrates a similar orthogonal resonator, where the evanescent wave probe is formed by a small metal loop connected between the center conductor edge and ground plane. When magnetic resonance is excited, this resonance destroys the symmetry of the driving mode, and some power is coupled to the orthogonal mode. As a consequence, the probe or tip will pick up the spin induction or absorption signal, which will be coupled out to the output transmission line and amplified by a low noise RF amplifier. A tip shielding structure for this microstrip resonator is shown in FIG. 4B In a second embodiment of the invention, two cancellation schemes are available. In an external cancellation scheme, two substantially identical transmission line resonators (either a coaxial line, as shown schematically in FIG. 5 or a microstrip resonator or cavity/waveuide resonator) are used with one equipped with the evanescent probe (tip, loop or aperture as described herein) to generate evanescent wave and interact with a sample. Optionally, each of two resonators is equipped with an evanescent probe, but only one probe is activated. In an external cancellation system 61, illustrated in FIG. 6, first and (phase shifted) second output signals from the first and second resonators, 62A and 62B, are received and processed by a summer or power combiner 65, for background signal cancellation, by an amplifier 67 and by a detector 69.

Figure 8:
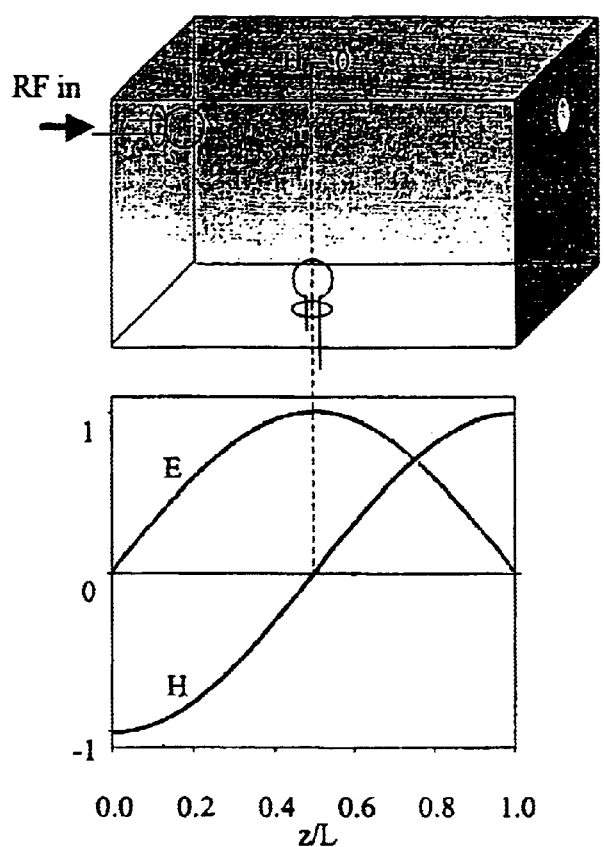

FIGS. 7A, 7B and 8 illustrate internal cancellation schemes (capacitive coupling, inductive coupling and cavity resonator types, respectively) and the corresponding electrical and magnetic fields, where the pickup coupling is positioned at the node of resonance mode of the resonator. As the evanescent probe excites spin resonance, the node condition is broken and pickup coupling then detects the desired spin resonance signal. Here, the probe may be a small aperture in the housing. In the inductive coupling and capacitive coupling modes in FIG. 7A, the magnetic field H and electrical field E, respectively, vanishes at the respective housing apertures, 71 and 72.

In another embodiment, illustrated in FIG. 7A, a node for a resonator or signal coupler is identified, where the signal vanishes or has a very small magnitude for a selected input frequency $f_{in}$ when no sample is present, for example the location marked "N." An output signal pickup module is then located the node point N, and an input signal with the frequency $f_{in}$ is applied to the coupler to produce an evanescent signal at a sample located adjacent to the probe. A spin resonance response from the sample breaks the symmetry, and a relatively large output signal is then sensed at the node point, representing the spin resonance response of the sample.

Figure 5:
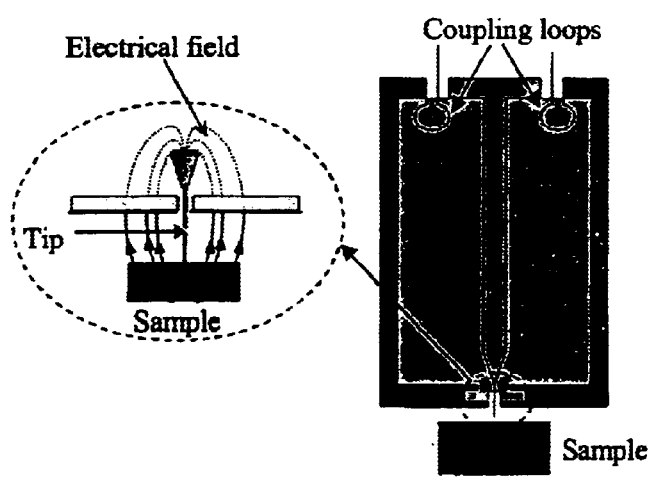
FIG. 5 schematically illustrates EMP apparatus.
Figure 6:
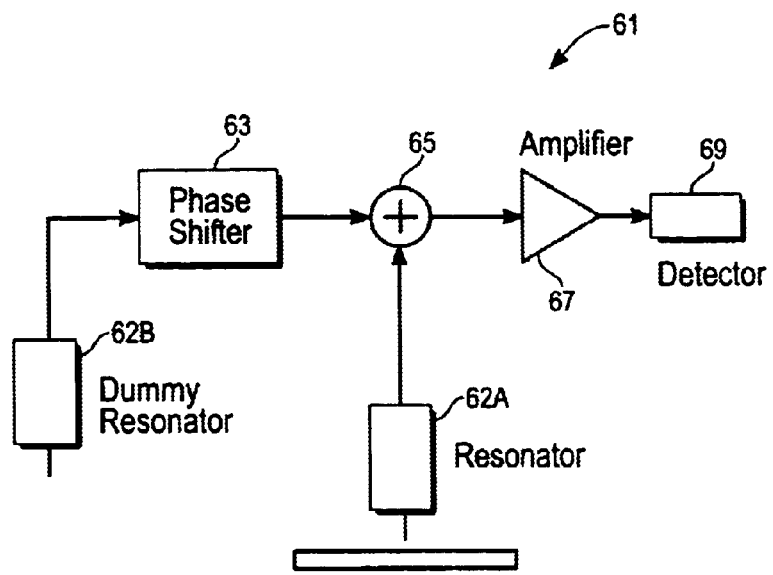
FIG. 6 schematically illustrates an external cancellation approach.
Figure 9:
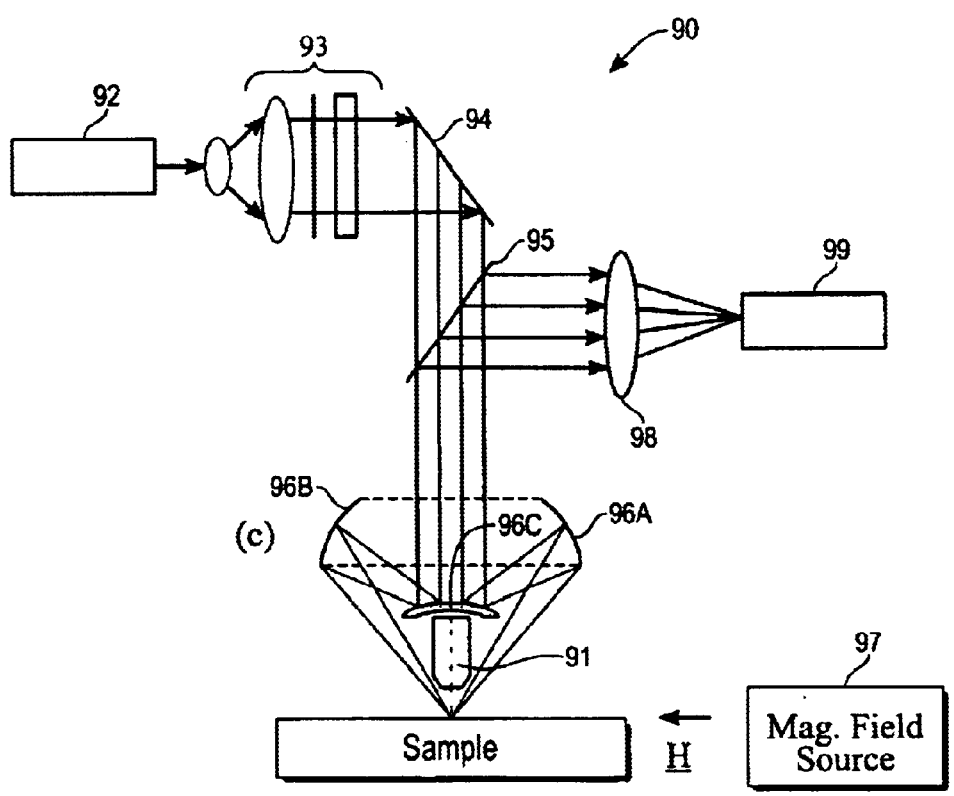
FIG. 9 schematically illustrates an optical pumping system, using a Schwartzschild optical objective, for use with an EMP approach.

In a third embodiment of the invention, fluorescence light is collected with the Schwarzschild optical objective and detected by a photodetector, as illustrated in the system 90 shown in FIG. 9. An evanescent microwave probe (EMP) 91 is used to excite the spin resonance in one version. The EMP can be made of a $\lambda/4$ transmission line resonator, as illustrated in FIG. 5 (a coaxial resonator or a microstrip resonator are two examples) with an electrically conducting tip connected to the central conductor or a loop connected between the center conductor and ground shielding, or cavity type resonator with an aperture type evanescent probe. To achieve better spatial resolution, the end-wall of the resonator can be shielded by a thin metal film with an aperture in transmission type resonator cases. A tip or loop for the probe extends beyond the shielding wall from the aperture. An EMP tip is used to provide microwave radiation and define the spatial resolution.

A laser beam is generated at a light source 92 and is processed by a first optical system 93, optionally including a lens and/or quarter-wave plate and/or a first linear polarizer. The processed beam is reflected by a first reflector 94, passes through a partly transmissive second reflector 95, and is received by several optical components, 96A, 96B and 96C, of a Schwartzschild objective that directs the laser beam toward the sample. A magnetic field source (dc or slowly swept in field strength) 97 provides a field H that is generally perpendicular to the direction of the EMP signal. Light scattered or generated at the sample is redirected by the Scwartzschild objective components, is mostly reflected by the second reflector 95, is received and processed by a second optical system 98, optionally including a second linear polarizer-analyzer, and is received and analyzed by a detector 99. In a first operating mode, the EMP signal provides sample excitation and the laser beam provides sample interrogation and sensing. In a second operating mode, the roles of the two signals are partly reversed.

By measuring the change of intensity or polarization of fluorescence light produced by the laser beam, one can obtain a spin resonance signal. Optical detection has very high sensitivity, which may allow one to achieve single spin detection. In order to achieve this high sensitivity, the cancellation of transmitted pumping light background is necessary. Transmitted light is usually circularly polarized, while the fluorescence light is usually linear polarized. A quarter-wave plate can be used to transform the circularly polarized transmitted light to linear polarized light, which is oriented at a right angle to the polarized direction of fluorescence light. In this case, a linear polarizer can be used to block the transmitted light and allow the fluorescence light to pass.

In a transmission type resonator with an evanescent wave probe, a shielding wall with an aperture, from which the probe (metal tip or loop) extends from the resonator and interacts with the sample, can be used to increase the spatial resolution.

Figure 10:
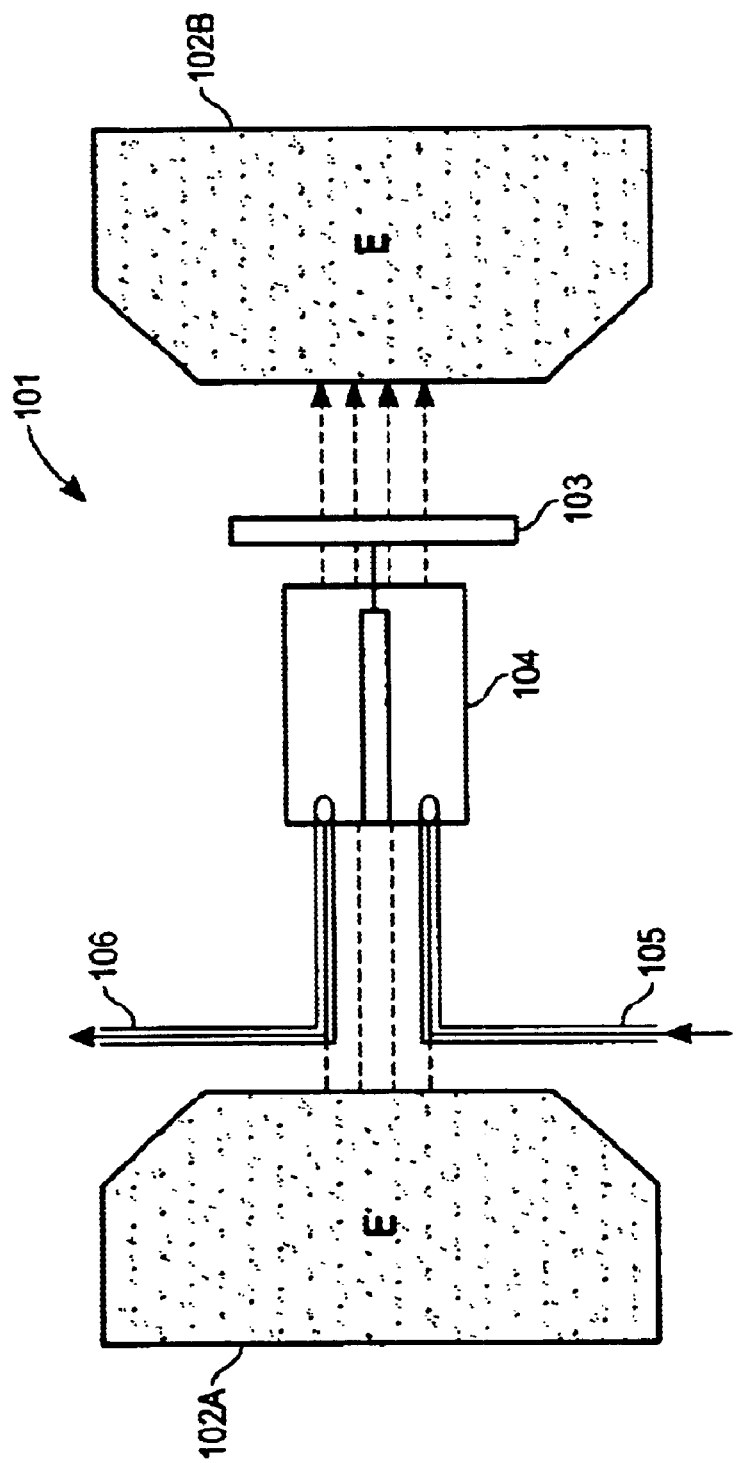
FIG. 10 schematically illustrates use of EMP apparatus for magnetic resonance detection.

We have performed a preliminary experiment to verify the fundamental principle of EMP detection of spin resonance. An experimental set-up 101 is illustrated in FIG. 10. Two spaced apart electromagnet poles, 102A and 102B, have a sample 103 positioned between them. An EMP probe 104, located adjacent to the sample 103, is fed by an RF signal source 105 and transmits evanescent waves to the sample. Spin resonance signals are detected by the EMP probe 104 and are transmitted by an RF signal output module to a suitable detector-analyzer.

A measurement of ferromagnetic resonance (FMR) of a YIG single crystal was conducted using an Evanescent Microwave Probe. The sample is a YIG single-crystal with a dimension of 4mm×4mm×0.5mm. The electromagnet has a 1.5" gap between a pair of 3" diameter poles. The shape of the poles was designed to have a magnetic field uniformity of about $10^{-5}$ in a 1 cubic inch sample volume at the center of the gap.

The measurements were made by attaching the sample to an EMP tip. The EMP resonator serves as a spin resonance excitation RF source as well as a detector. EMP microwave electronic and digital acquisition system measures the changes in cavity resonant frequency and quality factor Q while scanning the external magnetic field. When a ferromagnetic resonance condition is satisfied, a sample volume near the EMP tip will interact with EMP. This condition was detected by measuring resonant frequency $f_r$ and quality factor Q of the EMP resonator.

Figure 11A:
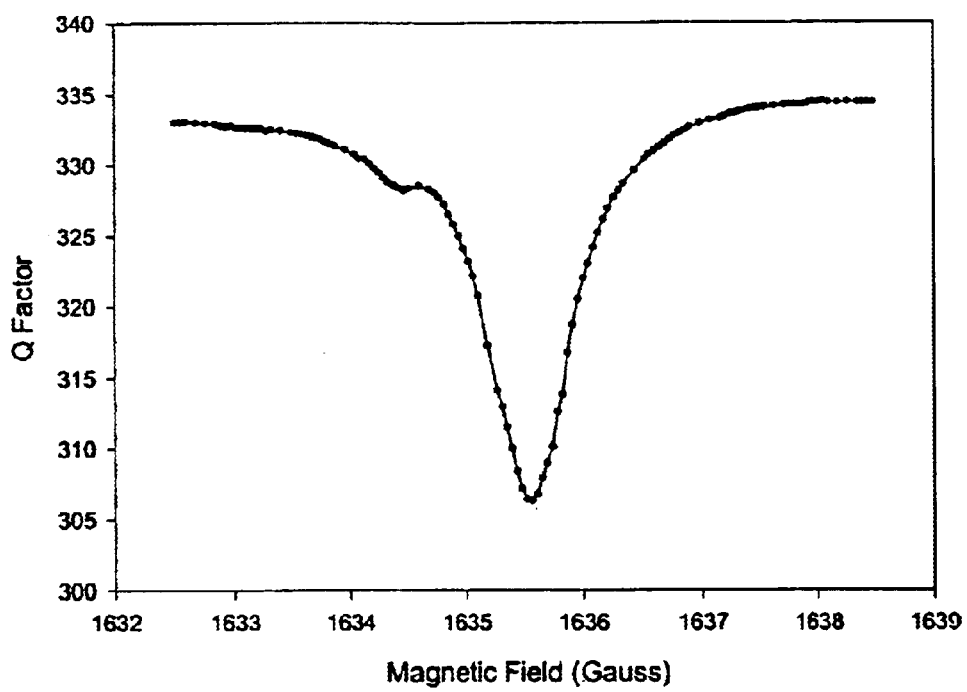
FIGS. 11A and 11B graphically EMP resonance and Q factor versus magnetic field strength H for a YIG sample.
Figure 11B:
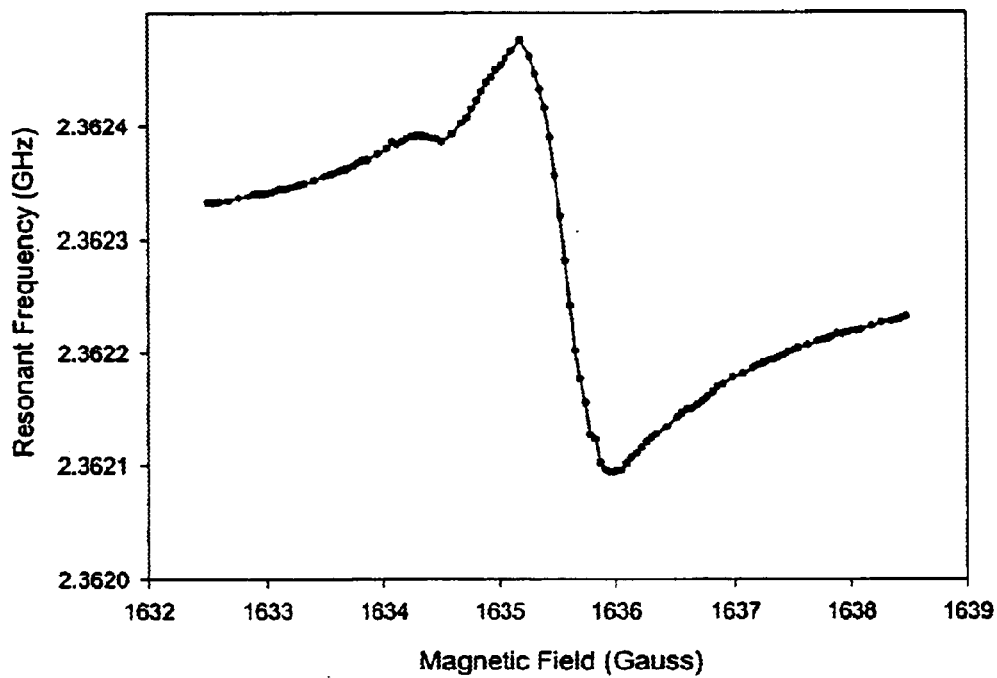

FIGS. 11A and 11B graphically illustrate FMR curves obtained by measuring the EMP resonant frequency and Q versus external magnetic field H. The relation between $f_r$ and H arises from changes in the propagation constant of the probe circuit that are caused by a dispersion influence of the real part of the permeability $\mu'$, according to a relation $$\mu' = 1 + \frac{\gamma 4\pi M(f-f_0)}{(f^2-f_0^2)+\gamma^2(\Delta H)^2} \quad (2)$$

$$\approx 1 + \frac{\gamma 4\pi M(f-f_0)}{\gamma^2(\Delta H)^2} \text{ (near resonance)}$$

where $f_0$ is the FMR frequency and $\gamma$ (=2.8 GHz/kOe) is the gyromagnetic constant. Absorption of microwave energy will reduce the Q factor of the probe through the resonance peak in the imaginary component $\mu''$, according to $$\mu'' = \frac{\gamma 4\pi M \gamma(\Delta H)}{(f^2-f_0^2)+\gamma^2(\Delta H)^2} \quad (3)$$

$$\approx \frac{\gamma 4\pi M}{\gamma(\Delta H)} \text{ (at resonance)}$$

The actual FMR condition is established when the proper Kittel relation is satisfied. In this experimental configuration, $$f_0 = \gamma\sqrt{H(H+H_{K+4\pi M})}, \quad (4)$$

where $H_K$ is the anisotropy field (~50 Oe) that is usually ignored when approximate values are sufficient.

Applications

Spatially resolved spin detection can be used to study a broad range of materials and biological specimens in much finer detail than has been available.

The technique can be used for high throughput screening of combinatorially synthesized compounds to identify specific chemical bonding and other spin resonance related signatures in the compounds.

Where ferromagnetic spin resonance is of interest, the invention provides a direct readout of real and imaginary parts of the RF permeability for extremely small specimen volumes of ferro- or ferrimagnetic materials. A line width associated with ferromagnetic resonance response (FMC) of a single crystal of yttrium-iron garnet (YIG), illustrated graphically in FIG. 11A, approaches the practical limit of less than 1 Oe at room temperature for commercially available chemical purity and crystal perfection. YIG and similar ferrimagnetic and ferromagnetic compounds can be used to "tag" a suitable target compound in order to more easily sense the presence or condition of the target compound.

Accurate measurement of the resonance frequency can be used to monitor small changes in specimen magnetization (magnetic moment/volume), magnetic anisotropy, mechanical strain (magnetostriction) and/or shape anisotropy. Magnetization and magnetic anisotropy are also very sensitive to temperature, and FMR probes have been investigated for use as thermometers. The peak of the resonance line is also proportional to the ratio of magnetization to intrinsic line width (for a Lorentzian shape spectrum). As such it sensitively characterizes variations in chemical composition, structural homogeneity, and polaronic charge from the magnitude of the circuit Q and the degree of Gossip line broadening.

Another important application is the detection of small (nm to $\mu$m size) ferromagnetic, super-paramagnetic, or light-pumped spin-populated semiconductor particles. These particles can be used, as fluorescent particles are currently used in bioscience, as tagging particles (when the appropriate chemical bonding is used to link the particle with molecules, pathogens, DNA's, proteins and other biological reagents) to diagnose or to identify structure, activity and other biological properties.

For this application, high sensitivity of the detection technique is extremely important. Because room temperature detection is crucial, high spin population of the particles and long spin relaxation time at room temperature are also important. Choice of materials for the tagging particles is, therefore, also important. The criteria for particle materials are narrow spin resonance (i.e., long relaxation ), high g factor, non-metallic and high ferromagnetic magnetization at room temperature. The high Q made possible by the narrow-line width specimens such as highest purity Yttrium Ion Garnet (YIG), YIG substituted with aluminum, gallium or indium, or certain spinel compounds such as lithium ferrite, are examples of suitable choices for the particle materials. Furthermore, changes in (narrow) line widths can also be used to sense changes induced by adsorbed magnetic molecules on the surface or chemical bonding. For this application, the largest practical surface-to-volume ratio is desirable. Ferrite materials, such as YIG, also has the advantages of non-air sensitive as in metallic particles, and robust ferromagnetic properties as particles size decreases. A ferrite molecule is attached to at least one molecule whose presence or absence in a collection of molecules is of interest, and a selected portion of the collection is interrogated using spatially resolved spin resonance detection. If spin resonance (1) is detected or (2) is not detected, this condition is interpreted as indicating that (1) the molecule of interest is present or (2) the molecule of interest is present, if at all, in a concentration that is below a detection threshold for the spin resonance detection, respectively.

Advantages of using detection of spin resonance of small particles, such as YIG or lithium ferrite, include the following:

1. Discrimination between specific bonding and non-specific bonding. Magnetic force of ferromagnetic particles and influence of spin resonance frequency (field) can all be used to discriminate between of specific and non-specific bonding.

2. Because different materials have different spin resonance (frequency-magnetic field relationship), this technique will provide "multi-color" capability as in a luminescent tagging technique. This response is in contrast to the magnetization detection technique for simple magnetic particle tagging, where only one property, magnetization, is measured and cannot be used to distinguish different types of tagging particles or agents.

What is claimed is:

1. A method for spatially resolved spin resonance detection in a material sample, the method comprising:

providing an excitation signal, having an excitation magnetic field with a selected excitation magnetic field direction in a sample, the excitation signal having at least one of a substantially static amplitude and a time varying amplitude with a selected frequency component $f_{exc}$;

providing an external magnetic field, having a magnetic field direction oriented substantially perpendicular to the excitation magnetic field direction and having selected magnetic field strength values at one or more locations, in a selected portion of the sample, where the external magnetic field has at least one of a substantially static field component and a time varying field component having a frequency that is substantially lower than said excitation frequency $f_{exc}$;

allowing the external magnetic field and the excitation field to interact with at least one spin for at least one atomic constituent in the selected portion of the sample, and to produce a spin resonance signal arising from the at least one spin;

using an evanescent wave probe, located adjacent to the sample, to perform at least one of (i) excitation and (ii) sensing of the spin resonance for the at least one spin, where the spin resonance signal is drawn from a group of resonance signals consisting of electron spin resonance, ferromagnetic resonance and nuclear magnetic resonance;

providing a sensing mechanism having a detection port to detect the spin resonance signal for the at least one spin;

providing a signal cancellation mechanism that suppresses presence of the excitation signal at the frequency $f_{exc}$ at the detection port when the spin resonance signal is sensed;

providing low noise amplification of the signal sensed after suppression of the presence of the excitation signal at the detection port; and detecting the amplified signal of the spin resonance as an output signal.

2. The method of claim 1, further comprising choosing said excitation frequency $f_{exc}$ in the radiofrequency or microwave range.

3. The method of claim 1, further comprising providing optical pumping for said selected portion of said sample to increase a spin population difference between a a spin-up state and a spin-down state for at least one of an electron and a nucleus at a selected temperature greater than 0° K.

4. The method of claim 3, further comprising:
providing an optical pumping arm for said optical pumping combined with an optical detection arm for detecting said spin resonance signal;
providing an optical pumping signal having a selected polarization state in the optical pumping arm;
detecting an optical signal in the optical detection arm resulting from interaction of the optical pumping signal, said excitation signal and said external magnetic field with said at least one spin in said sample;
analyzing the optical signal received in the optical detection arm, with a polarization analysis direction chosen to minimize an optical signal received from the optical pumping arm, when said external magnetic field is absent.

5. The method of claim 4, further comprising providing a Schwartzschild optical lens system for said combined optical pumping arm and said optical detection arm, integrated with said evanescent wave probe.

6. The method of claim 4, further comprising providing as said optical pumping signal an elliptically polarized optical signal that is passed through a wave plate to convert the elliptical polarization state to a linear polarization state.

7. The method of claim 6, further comprising providing a quarter-wave phase shifter and a first signal polarizer, having a selected first polarization direction, in said optical pumping arm;
providing in said optical detection arm a signal polarization analyzer, having a second polarization direction chosen to minimize an optical signal received from said optical pumping arm, when said external magnetic field is absent.

8. The method of claim 4, further comprising providing said optical excitation signal with a linear polarization state.

9. The method of claim 1, further comprising
providing an input signal coupler and an output signal coupler for a resonator, having a resonant frequency $f_{res}$ and being associated with said probe, and choosing said frequency $f_{exc}$ to be substantially equal to $f_{res}$.

10. The method of claim 9, further comprising providing said resonator as a cavity-type resonator and providing said evanescent wave probe as an aperture at a selected location in a shielding wall of said resonator.

11. The method of claim 9, further comprising locating said aperture at a position where a magnetic resonance field strength corresponding to said frequency $f_{exc}$ has an approximately maximum value.

12. The method of claim 9, further comprising choosing said resonator to be a transmission line-type resonator, comprising a center conductor connected to said evanescent wave probe.

13. The method of claim 12, further comprising drawing said resonator from a group of transmission line-type resonators consisting of a stripline, a microstrip line and a coaxial line resonator.

14. The method of claim 13, further comprising choosing said evanescent wave probe to comprise a small radius electromagnetic loop connecting said center conductor to a ground plane.

15. The method of claim 14, further comprising:
providing said resonator with electromagnetic shielding having a small aperture; and
locating at least a portion of said loop in the resonator aperture.

16. The method of claim 12, further comprising choosing said evanescent wave probe to comprise a small radius, electrically conducting wire with a tip having a small radius, connected to said center conductor.

17. The method of claim 16, further comprising:
providing said resonator with electromagnetic shielding having a small aperture; and
locating at least a portion of said tip in the resonator aperture.

18. The method of claim 1, further comprising:
providing an input signal coupler and an output signal coupler for a resonator, associated with said probe and having at least first and second degenerate orthogonal modes with an associated resonant frequency substantially equal to $f_{exc}$;
arranging for the input coupler and said probe to strongly couple to the first degenerate mode and for the output coupler to strongly couple to the second degenerate mode, when said external magnetic field is absent;
causing said probe to emit said excitation signal to said selected portion of said sample; and
sensing a non-zero portion of said output signal with frequency component $f_{res}$ at the output coupler, representing said interaction of said evanescent wave and said external magnetic field with said at least one spin.

19. The method of claim 18, further comprising:
adjusting at least one parameter associated with at least one of said input coupler, said output coupler and said resonator so that, when said external magnetic field is absent, an amplitude of said output signal received at said output coupler is minimized; and
sensing said spin resonance signal at said output coupler when said external magnetic field is provided at said sample.

20. The method of claim 18, further comprising providing said resonator as a stripline or microstrip resonator.

21. The method of claim 20, further comprising:
providing said resonator with a substantially square center conductor, and arranging for said input coupler to couple to a first edge of the conductor, and for said output coupler to couple to a second edge, orthogonal to the first edge, of the conductor;
choosing said evanescent wave probe to comprise a small radius, electromagnetic loop connecting the center conductor to an edge opposite the first edge of the conductor; and
choosing a dimension of each side of the center conductor to be $n\lambda$, where n is a selected non-zero integer and $\lambda$ is a wavelength corresponding to said excitation frequency $f_{exc}$.

22. The method of claim 20, further comprising:
providing said resonator with a substantially square center conductor, and arranging for said input coupler to couple to said probe and to a first edge of the conductor, and for said output coupler to couple to a second edge, orthogonal to the first edge, of the conductor;
choosing said evanescent wave probe to comprise a small radius, electrically conducting tip connecting the center conductor to an edge opposite the first edge of the conductor; and
choosing a dimension of each side of the center conductor to be $n\lambda/2$, where n is an odd integer and $\lambda$ is a wavelength corresponding to said excitation frequency $f_{exc}$.

23. The method of claim 20, further comprising:

providing said resonator with a substantially circular center conductor, having a diameter sufficient to support at least a pair of orthogonal degenerate modes corresponding to said frequency $f_{exc}$;

connecting said input coupler and said output coupler to first and second selected locations, respectively, spaced apart approximately $\pi/2$ radians, on a circumference of the circular conductor.

24. The method of claim 18, further comprising providing said resonator as a cavity-type resonator that supports at least a pair of orthogonal degenerate modes at said frequency $f_{res}$, and providing said evanescent wave probe as an aperture at a selected location in a shielding wall of said resonator, where a degenerate mode amplitude associated with said input coupler is much larger than a degenerate mode amplitude associated with said output coupler.

25. The method of claim 1, further comprising:

providing an input signal coupler and an output signal coupler for a resonator, associated with said probe and having at least one node point at a location not on a circumference of the resonator for an input signal with said frequency $f_{res}$;

providing said excitation signal to the input coupler, where said input signal produces an evanescent wave at said probe that is strongly coupled to the input coupler and the output coupler is coupled to the node point, when said external magnetic field is absent; and sensing a non-zero portion of said output signal with frequency component $f_{res}$ at the node point, representing said interaction of said evanescent wave and said external magnetic field with said at least one spin.

26. The method of claim 25, further comprising:

adjusting at least one parameter associated with at least one of said input coupler, said output coupler and said resonator so that, when said external magnetic field is absent, an amplitude of an output signal received at said output coupler is minimized; and sensing said spin resonance signal at said output coupler when said external magnetic field is provided at said sample.

27. The method of claim 1, further comprising:

providing first and second, substantially identical resonators, where the first resonator, but not the second resonator, is connected to said evanescent wave probe and is located adjacent to said sample of material;

providing said excitation signal along the first and second resonators to produce said evanescent wave;

forming a difference of first and second resonator output signal components for said frequency component $f_{res}$, representing said interaction of said evanescent wave and said external magnetic field with said at least one spin.

28. The method of claim 27, further comprising:

adjusting an amplitude and said resonant frequency of said second resonator so that a magnitude of said difference is minimized when said external magnetic field is absent; and sensing said difference of said first and second output signal components when said external magnetic field is provided at said sample.

29. The method of claim 1, further comprising providing, as said sample, at least one of a selected inorganic material, a selected organic material and a selected biological material;

obtaining and analyzing said spin resonance signal and determining at least one of the following characteristics associated with said spin resonance signal for the at least one selected material: a spin resonance energy, a spin resonance line width, a change in a spin resonance line width, a spin resonance relaxation time, a change in spin resonance relaxation time, magnetization, and at least one measure of temperature dependence of said spin resonance signal.

30. The method of claim 29, further comprising:

attaching a selected ferrimagnetic particle to said at least one molecule in said sample; and obtaining said spin resonance signal as a ferromagnetic resonance signal for the selected particle in said sample.

31. The method of claim 29, further comprising choosing said selected ferrimagnetic material from a group of materials consisting of yttrium-iron-garnet and lithium ferrite.

32. The method of claim 29, further comprising:

providing said characteristic of a spin resonance signal for a known ferrimagnetic material;

comparing said provided characteristic with a corresponding characteristic determined for said spin resonance signal obtained from said sample; and when said provided characteristic substantially agrees with said spin resonance signal characteristic obtained from said sample, interpreting this condition as indicating that at least one of the known ferrimagnetic material is present in said sample.

33. The method of claim 29, further comprising:

attaching a selected ferrimagnetic particle to said at least one material in said sample;

allowing said at least one material to chemically react with a second selected material in said sample to produce a third selected material; and obtaining said spin resonance signal as a ferrimagnetic resonance signal for the third selected material.

34. The method of claim 29, further comprising providing said sample with at least one of a protein, a DNA strand, an enzyme, a pathogen and a selected biological sample, as said selected material.

* * * * *